United States Patent [19]

Gold

[11] 4,444,195

[45] Apr. 24, 1984

[54] CARDIAC LEAD HAVING MULTIPLE RING ELECTRODES

[75] Inventor: Philip Gold, Pompano Beach, Fla.

[73] Assignee: Cordis Corporation, Miami, Fla.

[21] Appl. No.: 317,461

[22] Filed: Nov. 2, 1981

[51] Int. Cl.³ .......................... A61B 5/04; A61N 1/04
[52] U.S. Cl. .................................. 128/642; 128/786
[58] Field of Search ............................... 128/783-786, 128/419 P, 642, 348, 303.1, DIG. 9

[56] References Cited

U.S. PATENT DOCUMENTS

| | | | |
|---|---|---|---|
| 3,664,347 | 5/1972 | Harmjanz | 128/419 P X |
| 3,769,984 | 11/1973 | Muench | 128/419 P X |
| 3,788,329 | 1/1974 | Friedman | 128/786 |
| 3,825,015 | 7/1974 | Berkovits | 128/419 P X |
| 3,903,897 | 9/1975 | Woollons et al. | 128/642 X |
| 3,942,536 | 3/1976 | Mirowski | 128/419 D |
| 3,995,623 | 12/1976 | Blake et al. | 128/642 |
| 4,073,287 | 2/1978 | Bradley et al. | 128/642 |
| 4,144,889 | 3/1979 | Tyers et al. | 128/785 |

FOREIGN PATENT DOCUMENTS 7157   1/1980   European Pat. Off. ............ 128/784

Primary Examiner—Lee S. Cohen
Assistant Examiner—Angela D. Sykes
Attorney, Agent, or Firm—Henry W. Collins; Thomas R. Vigil

[57] ABSTRACT

A cardiac lead having ring electrodes positioned at predetermined locations along the length of the lead either for stimulating the heart at various selected locations, or for sensing electrical signals generated at various selected locations within the heart. The cardiac lead includes an insulative tubing having a plurality of pairs of apertures positioned at selected locations along the length of the tubing. A plurality of conductors are positioned within the tubing and extend through respective ones of the pairs of apertures. A plurality of ring electrodes are each positioned to cover a pair of apertures. The ring electrodes are mechanically bonded to the insulative tubing and are electrically connected to the conductors.

5 Claims, 4 Drawing Figures

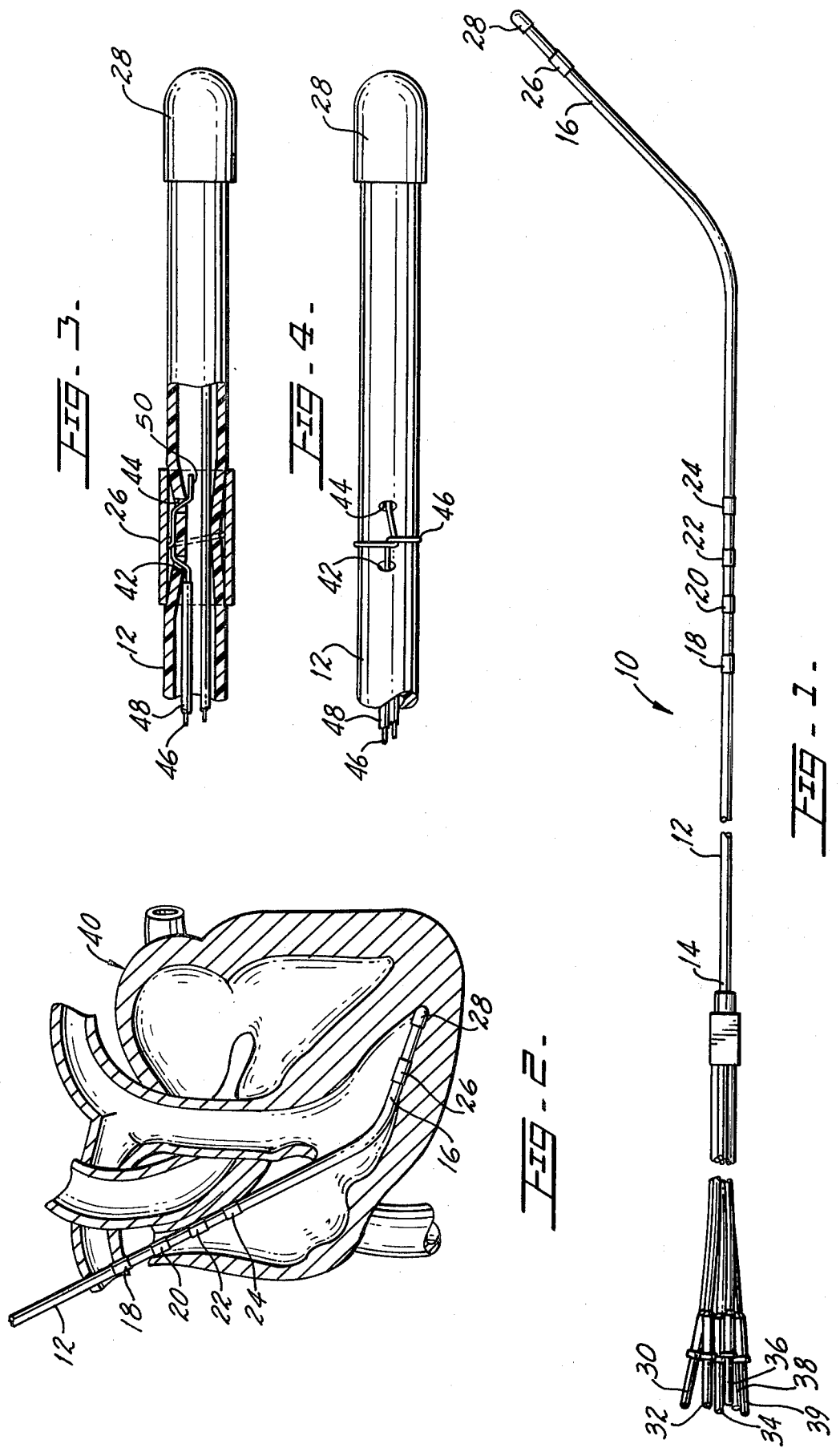

CARDIAC LEAD HAVING MULTIPLE RING ELECTRODES

DESCRIPTION OF THE INVENTION

Multiple electrode cardiac pacing leads are well known and have been utilized for pacing both the atrial and ventricular chambers of the heart. In addition, multiple conductor leads have been placed within the heart in order to measure voltage signals which exists at various regions within the cavities of the heart.

Cardiac stimulation requires a reliable means for connecting electrical signals from a pulse generator, or pacer, to a pre-selected region on the wall of the heart. Similarly, cardiac monitoring requires a reliable means for connecting a voltage sensing device to a selected region, or regions, on the wall of the heart. For example, a certain type of cardiac pacing lead is connected to a pacer, extends into the heart, and is placed in contact with the inside wall of the right ventricle. This lead normally takes the form of long, generally straight, flexible, insulated conductor having one end electrically connected to the pacer and the other end connected to an electrode. The electrode is placed in contact with the wall of the heart.

On the other hand, pacing leads which are used for stimulation of the atrium are generally formed in a J-shaped configuration so that when the lead is inserted through a blood vessel and into the heart, the lead may be positioned to curve up into the atrial cavity. One problem associated with placing a pacing lead in the atrium is caused by the fact that the atrium has relatively smooth wall surfaces. With these smooth surfaces, it is difficult to retain the electrode in a fixed position with respect to the wall of the atrium.

In dual chamber pacing, it is necessary to place a first electrode in contact with the wall of the atrium and a second electrode in contact with the wall of the ventricle. Generally, a ventricular lead is passed through a blood vessel and into the ventricular cavity. When the ventricular pacing lead has been stabilized within the heart, a second lead, or atrial lead, is passed through the blood vessel and is moved into a selected position within the atrial cavity. As may be appreciated, the placement of two separate pacing leads into two separate chambers of the heart is a relatively complicated procedure due to the fact that as the second lead is being inserted, it is possible to strike the first lead with the second lead thereby dislodging the first lead.

The present invention takes the form of a single, very flexible, multiple electrode pacing lead which may be positioned within the heart so that one or more of the electrodes may be utilized to apply stimulating pulses to the ventricle and one or more of the electrodes may be utilized to apply stimulating pulses to the atrium.

With the concept of multiple electrodes being placed at predetermined locations along the length of the pacing lead, it is possible to carry out dual chamber pacing of the heart regardless of the spacing between the walls of the two chambers of the heart. In other words, selected ones of the multiple electrodes are chosen to stimulate selected regions within the heart. In addition, the cardiac lead of the present invention may be utilized to provide sensing, or mapping, of various regions of the heart including regions associated with both the atrial and the ventricular cavities. It is therefore possible to simultaneously monitor cardiac activity at various positions within both chambers of the heart with the lead of the present invention.

SUMMARY OF THE INVENTION

The body implantable lead of the present invention includes an elongated, flexible, insulative tubing which has multiple pairs of closely spaced apertures extending through the wall of the tubing at predetermined positions along the length of the tubing. Positioned within the insulative tubing are a plurality of flexible electrical conductors. Each of the electrical conductors has an insulative coating which surrounds a conductive wire over the entire length of the conductor except for proximal and distal terminal portions. The proximal terminal portion of each of the electrical conductors is connected to an electrical connector which is adapted for connection to a tissue stimulating or monitoring device. The distal terminal portion of each of the electrical conductors extends out of the insulative tubing through one of the apertures in a pair of apertures is looped around the tubing and then extends over or under the loop and back into the tubing through the other aperture. Multiple ring electrodes are each positioned to cover a corresponding pair of apertures and are mechanically bonded to the tubing as well as electrically bonded to the distal terminal portion of a corresponding electrical conductor.

In a preferred form, each of the ring electrodes takes the form of a hollow cylindrical cylinder having an outside diameter which is approximately the same outside diameter as that of the insulative tubing to thereby provide a relatively smooth surface along the length of the lead.

In still another embodiment of the present invention, the spacing between at least two of the ring electrodes is equal to approximately six centimeters so that one of the electrodes may be used to stimulate or monitor cardiac activity in the atrial cavity and the other ring electrode may be used to simultaneously stimulate or monitor cardiac activity in the ventricular cavity. Various ones of the multiple electrodes may be selected to stimulate or monitor cardiac activity at various regions within the two chambers of the heart.

BRIEF DESCRIPTION OF THE DRAWINGS

FIG. 1 is an elevational view of the multiple electrode cardiac lead of the present invention;

FIG. 2 is a cross-sectional view of the heart with the multiple electrode cardiac lead of the present invention positioned to stimulate and/or monitor various regions within the chambers of the heart; and, FIG. 3 is an elevational view shown partly in cross-section of the cardiac lead of FIG. 1 and illustrates in more detail the construction of the ring electrodes of the present invention.

FIG. 4 is a top view of a portion of the cardiac lead of FIG. 1 with the ring electrode removed and illustrates in more detail the connection to the ring electrode.

DESCRIPTION OF THE PREFERRED EMBODIMENT

Reference is now made to FIG. 1 which illustrates an elongated, flexible, multiple electrode cardiac lead 10. The cardiac lead 10 includes an insulative tubing 12 having a proximal end 14 and a distal end 16. Five ring electrodes 18, 20, 22, 24 and 26 are positioned at predetermined locations along the insulative tubing 12. A tip electrode 28 is positioned at the distal end 16 of the lead 10. The electrodes are connected through electrical conductors to the connector terminals 30, 32, 34, 36, 38 and 39. The connector terminals 30–39 are adapted to be connected to a cardiac pacer, or alternatively, to a cardiac monitor.

FIG. 2 generally illustrates a human heart 40 in cross-section with the cardiac lead 10 positioned to stimulate both the ventricle and atrium. In the position as shown, a selected one, or both, of the ring electrodes 26, 28 may be utilized to stimulate the ventricle and either a selected one, or both, of the ring electrodes 22, 24 may be utilized to stimulate the atrium. Alternatively, the ring electrodes 26, 28 may be utilized to monitor cardiac activity at different locations within the ventricular cavity and ring electrodes 22, 24 may be utilized to monitor cardiac activity at two different locations within the atrial cavity.

As is apparent from FIG. 2, the lower portion, or distal end 16, of the cardiac lead 10 serves to stabilize the position of the ring electrodes 18, 20, 22 and 24 which are positioned in the atrial cavity. Accordingly, it is possible to stimulate either one or both chambers of the heart by use of the single cardiac lead 10. Alternatively, the single lead 10 may be utilized to monitor cardiac activity of various regions in either one or both of the chambers of the heart.

FIGS. 3 and 4 illustrate in more detail the construction of the cardiac lead 10 and the construction of the ring electrodes and the internal electrical conductors. More particularly, a pair of apertures 42, 44 extend through the wall of the tubing 12 at a selected position. An electrical conductor 46 includes an insulative coating 48 which extends along substantially the entire length of the electrical conductor except for a distal terminal portion 50 of the conductor 46. The electrical conductor 46, as are all of the other five electrical conductors, is positioned within the insulative tubing 12. The terminal portion 50 of the electrical conductor 46 extends through one aperture 44 of the pair of apertures 42, 44 to a position outside of the tubing 12. The terminal portion 50 then extends around the circumference of the tubing 12, and is twisted back around itself and then extends through the other aperture 42 to the inside of the tubing. Each of the other electrical conductors 18, 20, 22, 24 and 26 are arranged in a similar manner and include terminal portions which extend out of an aperture in the tubing 12, extend around the circumference of the tubing 12, twist back on themselves and extend through the other aperture into the tubing 12.

The ring electrode 26, which takes the form of a thin, hollow cylindrical conductive ring, is then positioned to cover the pair of apertures 42, 44, and is mechanically bonded to the insulative tubing 12 and electrically bonded by a compression fit to the terminal portion 50 of the electrical conductor 46. Alternatively, silver conductive epoxy may be interposed between the ring electrode, 42, 44 and the tubing 12 to provide an added mechanical and electrical bond between the elements. The other ring electrodes 18, 20, 22 and 24 are each positioned to cover a pair of apertures and to connect to a corresponding terminal portion of a conductor.

The outside diameter of the cylindrical ring conductor 26 is approximately equal to the outside diameter of the tubing 12 to thereby provide a relatively smooth outer surface over the entire length of the cardiac lead 10.

The resultant product is a cardiac lead which is very flexible and which has a smooth outer surface along the entire length of the lead. In addition, the electrical conductors are securely bonded to the insulative tubing to the ring electrodes.

Various modifications may be made to the cardiac lead of the present invention without departing from the spirit and scope of the invention. For example, the electrodes may be positioned at any desired locations along the length of the lead. In addition, an almost unlimited number of electrodes may be placed on the lead. Still further, various combinations of electrodes may be connected in common to a single conductor or the electrodes may each be connected to a separate electrical conductor. With the arrangement of the present invention, broad flexibility may be obtained in either pacing or monitoring of activity in either one, or both chambers of the heart.

What is claimed is:

1. An endocardial lead comprising:

an elongated, flexible electrically insulative tubing having proximal and distal ends and an outer surface, said insulative tubing having at least one pair of closely spaced apertures extending through the wall of the tubing at predetermined positions intermediate said proximal and distal ends;

at least one elongated, flexible, electrical conductor positioned within the insulative tubing and extending for substantially the entire length of the insulative tubing, said electrical conductor having an insulative coating surrounding the electrical conductor over substantially the entire length thereof except for proximal and distal terminal portions;

the proximal terminal portion of said electrical conductor being connected to an electrical connector adapted for connection to a tissue stimulating or monitoring device;

the distal terminal portion of said electrical conductor extending out of one aperture of said pair of apertures in said insulative tubing, first axially forwardly, second around the circumference of the tubing defining a loop, third under or over the axially forwardly extending portion of said conductor and fourth axially forwardly over or under the loop to and into the other aperture, whereby said electrical conductor is fixed in a knot formation at the distal end thereof in such a manner as to prevent the pulling out of said conductor from said tubing; and, at least one metal sleeve defining a ring electrode on the outer surface of said insulative tubing, said metal sleeve having an inner surface and being frictionally received over said insulative tubing and positioned over said at least one pair of apertures having an electrical contact surface on the inner surface of the at least one metal sleeve in contact with said distal terminal portion of said conductor whereby, when said metal sleeve is frictionally received over said insulative tubing and positioned over said at least one pair of apertures, said contact surface presses against and makes electrical contact with said distal terminal portion of said conductor between said pair of apertures.

2. The endocardial lead of claim 1 comprising a second metal sleeve defining a ring electrode on the outer surface of said insulative tubing, said second metal sleeve having an inner surface being frictionally received over said insulative tubing and positioned over a second pair of apertures having an electrical contact surface on the inner surface of the second metal sleeve in contact with the distal terminal portion of a second elongated conductor and wherein said ring electrodes are spaced apart approximately six centimeters on said tubing.

3. The endocardial lead of claim 1 wherein the outside diameter of said ring electrode is approximately equal to the outside diameter of said insulative tubing.

4. The endocardial lead of claim 1 wherein one of said apertures of said at least one pair of apertures is spaced axially forward of the other of said apertures.

5. The endocardial lead of claim 1 comprising a silver epoxy that is inserted between said metal sleeve and said insulative tubing to bond said metal sleeve to said exposed distal terminal portion of said conductor.

* * * * *